United States Patent [19]

Jung

[11] Patent Number: 4,616,643

[45] Date of Patent: Oct. 14, 1986

[54] DISPOSABLE EAR PROTECTOR

[76] Inventor: Ha Y. Jung, 3436 Carriage Cir., T 1, Randallstown, Md. 21133

[21] Appl. No.: 760,889

[22] Filed: Jul. 31, 1985

[51] Int. Cl.$^4$ ............... A41D 21/00; A61F 11/00
[52] U.S. Cl. ................................. 128/151; 2/174; 2/209
[58] Field of Search ............ 128/151, 154; 2/174, 2/209

[56] References Cited

U.S. PATENT DOCUMENTS

| | | | |
|---|---|---|---|
| 1,619,772 | 3/1927 | Thompson | 128/151 |
| 2,804,695 | 9/1957 | Scott | 2/174 X |
| 3,528,416 | 9/1970 | Chamberlain | 128/154 |
| 3,841,325 | 10/1974 | Pickard | 128/151 |
| 4,134,153 | 1/1979 | Voorhees | 128/151 X |
| 4,308,623 | 1/1982 | Voorhees | 128/151 X |
| 4,408,605 | 10/1983 | Doerr et al. | 128/151 X |

Primary Examiner—Richard E. Gluck
Attorney, Agent, or Firm—Birch, Stewart, Kolasch & Birch

[57] ABSTRACT

A disposable ear protecting device which comprises a cap, an absorbent pad having an intensive water-absorbing portion in the cap and a aperture having an adhesive portion having a masking cover, whereby the ear protecting device is utilized to the ear for precluding entry of the foreign matter including moisture. The ear protector is inexpensive, simplicity of manufacture and complete seal.

3 Claims, 3 Drawing Figures

DISPOSABLE EAR PROTECTOR

BACKGROUND AND FIELD OF THE INVENTION

The present invention relates to a disposable ear protector, and more particularly, to a water-proof ear cap to protect the ear from being exposed to the moisture of a shower room, a bath room or a swimming pool.

Many types of ear protectors utilizing an adhesive material for adhering the protector to the skull at the base of the ear are known. For example, U.S. Pat. No. 4,134,153 to Voorhees discloses a throw-away ear protector which employs a single large plaque of plastic material assembled over the ear by gathering it from its opposite sides. Thereafter all edges are gathered together about the ear and secured through the application of a rubber band, a twist wire or like. Because it is very difficult to apply to the ear, the gathered material can readily leak or become loose at an inopportune time and thus expose the ear to serious hazards. Furthermore, if the ear is exposed to moisture, as above-mentioned, there is no way to protect the ear from water penetrating thereinto. Also, U.S. Pat. No. 4,308,623 to Voorhees, discloses a disposable fluid-tight ear protector which comprises a wide and flat envelope which is closed except for a single opening sized to receive the outer ear. Assembly of the envelope about the ear is aided and facilitated by providing its opposite edges with inwardly extending pleats receptive of the user's forefingers and thumbs to grasp the envelope closely adjacent the exposed adhesive material while guiding the ear through the opening Thereafter the pleats enable the forefingers to press the ringlet of adhesive firmly against the skull leaving the ear fully enclosed in a snug fitting fluid-tight enclosure. However, the patent has the disadvantages and the inconvenience that the opposite edes of the ear protector is provided with inwardly extending pleats which are receptive of the user's forefingers and thumbs for grasping the envelope adjacent the exposed adhesive material. Furthermore, if the attaching operation is not performed with due care, the introduction of moisture into the ear cannot be avoided, which is a very serious problem for patients who have ear infections and diseases.

OBJECTS AND SUMMARY OF THE INVENTION

Accordingly, it is an object of the present invention to provide an improved disposable ear protector containing a hollow water-absorbing pad for enclosing and protecting the ear to completely preclude the entry of moisture thereinto.

Another object of the present invention is to provide a disposable water-proof ear cap having an outward extending adhesive surface which can be assembled about the ear easily and conveniently.

A further object of the present invention is to provide an inexpensive single use cap which is constructed with a size similar to that of the human ear and made of flexible materials such as polyvinyl chloride, polyolefine, e.g., polyethylene, soft rubber, or the like to look good.

Other objects and further scope of applicability of the present invention will become apparent from the detailed description given hereinafter. It should be understood, however, that the detailed description and specific examples, while indicating preferred emobidments of the invention, are given by way of illustration only, since various changes and modifications within the spirit and scope of the invention will become apparent to those skilled in the art from this detailed description.

The present invention provides an improved disposable ear protector which is inexpensive and simple to manufacture, easy to apply and includes a hollow, water-absorbing pad having an intensive water-absorbing portion disposed at center thereof for precluding the entry of moisture or like into the ear.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PRESENT INVENTION

Figure 1:
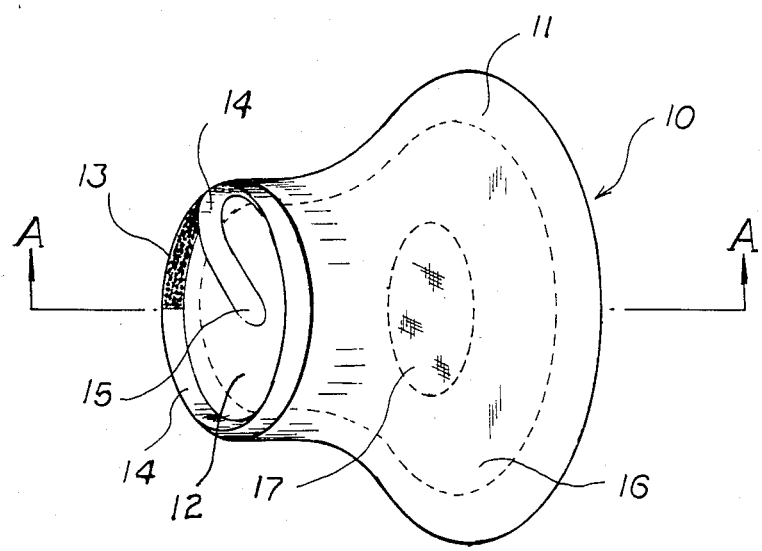
FIG. 1 is a perspective view of an illustrative embodiment of the disposable ear protector of the present invention.
Figure 2:
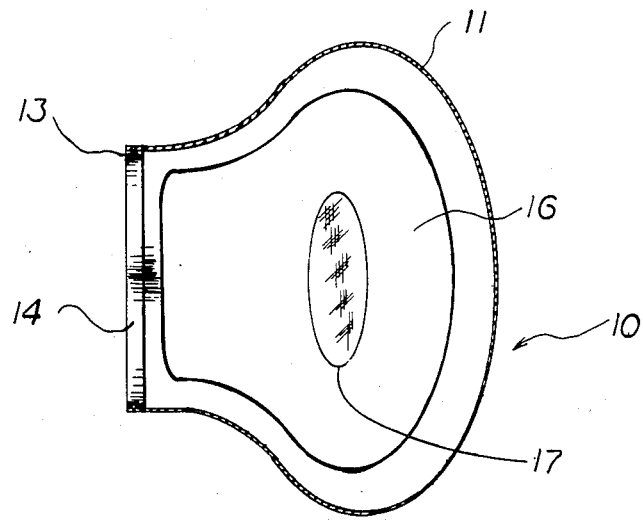
FIG. 2 is a cross sectional view taken along line A—A of FIG. 1 of the present invention.

Referring now in detail to the drawings for the purpose of illustrating the present invention, the disposable ear protector 10 of the present invention as shown in FIG. 1 comprises a cap 11, an aperture 12 for receiving the ear, a pressure sensitive adhesive portion 13 disposed at end of an inner side of the aperture 12, a masking cover 14 disposed on the adhesive portion 13 having a thumb tab 15 disposed at the end thereof and a pad 16 containing a more intense water-absorbing portion 17 located at center thereof which corresponds to the hole of the ear.

The cap 11 of the ear protector 10 of the present invention is conveniently formed from a seamless thermoplastic or rubber material having a cap or bag configuration. The various rubbers and thermoplastic materials which are suitable for use in practicing the present invention because of their imperviousness to moisture include, for example, polyvinyl chloride, polyolefine, for example, polyethylene, soft rubber, for example polybutadiene, and the like. The diameter of the aperture 12 corresponds to the size of the ear and thus can be elongated for closely mating with the human ear. The adhesive portion 13 is a pressure sensitive adhesive which is obtained from The Mercury Label Company and is harmless to the human skin. The pad 16 is made of cottons, polyesters, crosslinked polyelectrolytes or the like for absorbing moisture. The materials used as the intensive water absorbing portion 17 are made of polyamidopolyamine epichlorohydrin or polyalkylene glycol or the like which functions as the last and strongest protection in precluding water from entering the ear. Accordingly, if the protector 10 is not effective, the patient's ear can still be protected from the introduction of moisture into the ear.

In operation, after taking off the masking cover 14 by using the thumb tab 15 to expose the adhesive portion 13 of the cap 11, the cap 11 is attached to the ear utilizing the fingers to press the area behind of the adhesive portion 13 to seal the protector 10 to the skull surrounding the base of the ear. At that time, the pad 16 in the cap 11 closely surrounds the ear and more particularly, the water-absorbing portion 17 is positioned adjacent the hole of the ear in order to move completely preclude the entry of the moisture.

Figure 3:
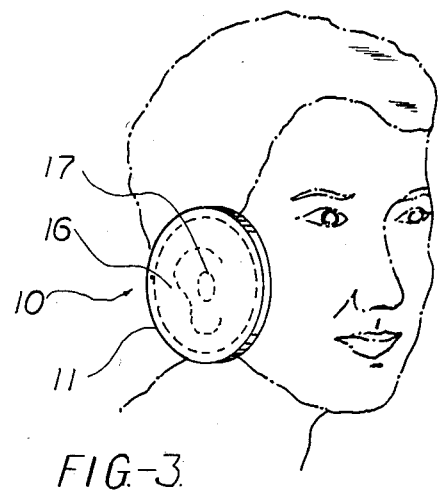
FIG. 3 is a perspective view showing one of the ear protectors of the present invention attached to a person's ear.

As shown in FIG. 3, the disposable ear protector of the present invention also has a related attractive appearance. The protector 10 is inexpensive because of simplicity of manufacture. The entire outer ear can now be sealed by the impervious cap 11 and all foreign matter in the form of a solid or a liquid can be prevented from entering the ear. Accordingly, patients with ear diseases may proceed to wash and dress their hair, take showers or even go swimming withoug fear or risk of moisture entering into the ear.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A disposable ear protecting device comprising:
   a cap portion for enclosing the ear, said cap portion provided with an aperture therein,
   an adhesive material disposed on the lip of the aperture,
   a masking material removably disposed over the adhesive material,
   an absorbent pad disposed in said cap, said pad containing a highly moisture absorbent portion located in the central position thereof and adapted to be positioned adjacent to and correspond in size to the hole in the ear.

2. A disposable ear protector of claim 1, wherein the adhesive material is designed to outwardly attached to the skull surrounding the ear.

3. The disposable ear protector of claim 1, wherein the highly moisture absorbing portion is made of a material selected from the group consisting of polyamidopolyamine epichlorohydrin and polyalkylene glycol.

* * * * *